(12) United States Patent  
Hargabus

(10) Patent No.: US 8,085,410 B1
(45) Date of Patent: Dec. 27, 2011

(54) PROJECTED SCANNING LASER DEVICE AND METHOD FOR LOCATING SMALL OBJECTS

(76) Inventor: Patrick Allen Hargabus, Sarasota, FL (US)

( * ) Notice: Subject to any disclaimer, the term of this patent is extended or adjusted under 35 U.S.C. 154(b) by 261 days.

(21) Appl. No.: 12/425,367

(22) Filed: Apr. 16, 2009

(51) Int. Cl.
*G01B 11/14* (2006.01)
(52) U.S. Cl. ........................................... 356/614
(58) Field of Classification Search .... 356/237.1–241.6, 356/242.1–243.8, 426–431, 600–640
See application file for complete search history.

(56) References Cited

U.S. PATENT DOCUMENTS

| | | | |
|---|---|---|---|
| 3,713,614 A * | 1/1973 | Taylor | 248/632 |
| 3,820,903 A * | 6/1974 | Kindl et al. | 356/138 |
| 4,476,607 A * | 10/1984 | Ross | 15/339 |
| 5,055,666 A * | 10/1991 | Miyahara | 250/206.1 |
| 5,208,438 A * | 5/1993 | Underberg | 219/121.78 |
| 5,889,479 A * | 3/1999 | Tabel | 340/958 |
| 5,967,645 A * | 10/1999 | Anderson | 362/259 |
| 5,979,766 A * | 11/1999 | Rockstein et al. | 235/462.46 |
| 6,163,969 A * | 12/2000 | Jan et al. | 33/282 |
| 6,171,018 B1 * | 1/2001 | Ohtomo et al. | 404/84.5 |
| 6,415,051 B1 * | 7/2002 | Callari et al. | 382/154 |
| 6,749,166 B2 * | 6/2004 | Valentine et al. | 248/309.1 |
| 6,941,665 B1 * | 9/2005 | Budrow et al. | 33/286 |
| 7,269,907 B2 * | 9/2007 | Levine et al. | 33/286 |
| 7,487,596 B2 * | 2/2009 | Nash | 33/290 |
| 7,797,844 B2 * | 9/2010 | Hobden et al. | 33/286 |
| 2004/0172839 A1 * | 9/2004 | Zirk et al. | 33/451 |
| 2004/0187327 A1 * | 9/2004 | Levine | 33/286 |

* cited by examiner

*Primary Examiner* — Gregory J Toatley
*Assistant Examiner* — Jarreas C Underwood
(74) *Attorney, Agent, or Firm* — Dorothy S. Morse

(57) ABSTRACT

A projection laser scanner and method used to locate otherwise difficult-to-see items inadvertently dropped onto relatively flat surface areas, such as but not limited to, floors, countertops, and tabletops, which uses a laser beam with a broad field of view to illuminate items raised above the surface area, giving each a glowing appearance. Should surface areas comprise raised features, the laser beam will illuminate them. However, dropped items thereon will still be very evident and remain easy to locate. Safety applications of the projection laser scanner are many, and include but are not limited to, finding dropped medication, small tools, eyeglass screws, contact lenses, pins, needles, staples, and other objects that one would not want a small child or pet to find and swallow; broken glass or ceramic shards; rings, earrings, and gemstones inadvertently separated from jewelry; as well as countless other difficult-to-see items that blend into background surface areas.

19 Claims, 3 Drawing Sheets

PROJECTED SCANNING LASER DEVICE AND METHOD FOR LOCATING SMALL OBJECTS

CROSS-REFERENCES TO RELATED APPLICATIONS

None.

BACKGROUND

1. Field of the Invention

This invention generally relates to devices used to find difficult-to-see small objects after they have been accidentally dropped or are otherwise lost, and specifically refers to a projection laser scanning device and method of its use wherein it can be set down upon, or held closely against the top of a surface area that is relatively flat (level or not), such as but not limited to a floor, countertop, tabletop, and the like, and wherein after the activation of its on-off or momentary switch, the present invention projection laser scanner creates a laser beam of light with a broad field of view that is projected substantially parallel to the relatively flat surface area and just above it, to illuminate all raised items in its path and give each a glowing appearance, making them instantly identifiable for prompt recovery. For efficiency and nearly immediate object recovery, the laser beam must illuminate a broad area. However, it is not critical whether the laser module of the present invention creates the glowing effect via use of a lens cap that broadens a laser dot into a line, or via use of a dot laser that is spinning or being moved in a sweeping action back and forth across its field of view. Furthermore, use of the present invention projection laser scanning device does not present a safety risk to eyes during its proper use, as it is employed very close to a surface area that is in a lowered position relative to the user's eyes. Should a surface area upon which a small object has been dropped and needs prompt recovery be close to a persons' eyes, the object would be more readily visible and use of the present invention would not likely be needed. Areas adjacent to the original path illuminated by the present invention projection laser scanner can also be quickly and easily viewed for the presence or absence of small raised objects by a user moving the laser beam of light with a broad field of view to the left or right toward them. Thus, with use of the present invention, the locations of inadvertently dropped items that would otherwise be camouflaged and hidden from view by colored/patterned surroundings, become instantly identified as a result of a vivid and brilliant illuminated appearance created as the laser beam of light with a broad field of view scans across them. Although not critical, a red laser is preferred, as it creates a very vivid illumination effect. If the relatively flat surface area upon which a small item has fallen has no raised surface texture or other surface irregularity, no part of that relatively flat surface area will be illuminated, and only the dropped item or items on it will have a glowing appearance. In the alternative, should the surface area upon which a small item has fallen have some raised feature or irregularity, the raised features and irregularities present will also be illuminated by the present invention laser beam of light, however, the small item or items being sought will also be very evident, instantly recognizable, and easy to retrieve. There are many important safety applications of the present invention projection laser scanner, which include but are not limited to, finding dropped medication, vitamins, contact lenses, eyeglass screws, small tools, pins, needles, push pins, coins, beads, staples, paper clips, and other objects that one would not want a baby, small child, or pet to find and swallow; broken glass or ceramic shards that could cause injury to people and pets; expensive rings, earrings, and/or gemstones inadvertently separated from jewelry that a small child or pet could also find and swallow; and countless other items that can easily blend into and become camouflaged by background surfaces. In addition, although not limited thereto, the projection laser scanner device of the present invention can optionally have a magnet in its housing usable for mounting the housing for ready accessibility against the front or side of a refrigerator, other kitchen appliance, metal desk or file cabinet, and the like. Also, or in the alternative, a magnet can be incorporated into the housing to assist a user in easily picking up small metal items located by the present invention's laser beam of light. The present invention projection laser scanner device may also optionally possess one or more LED or other light sources that can be used as a flashlight for a user to employ in searching for difficult-to-see small items where the surface onto which they have been dropped is too rough and/or uneven for satisfactory use of the present invention's laser beam of light with a broad field of view. Another useful but optional feature of the present invention is a low-power indicator light useful in making certain the device has fresh batteries when needed. Furthermore, in addition or in the alternative to having a magnet associated with its housing, the present invention projection laser scanner housing may optionally be connected to a keychain, lanyard, or even a walking cane or stick, so that it can be easily carried and employed by its user.

2. Description of the Related Art

Many hazards are present in the home and elsewhere, which can be quickly remedied by use of the present invention, and for which no other device is presently known to have equal advantage. For example, people often drop small items inadvertently onto floors, table tops, and other surface areas only to realize that the dropped item or items have scattered and/or bounced unpredictably away from the original impact area, making them difficult to retrieve. The inadvertently dropped item may be medication, vitamins, a contact lens, an eyeglass screw, a pin, a needle, a ring or earring, a gemstone from jewelry, a bead, a push pin, paperclip, a coin, staple, a broken piece of glass or china, or other object that one would not want a baby, small child, or pet to find and either step on or swallow. If the item is not sharp and otherwise does not pose a risk of contact injury to a hand, one can bend over or stoop down close to the surface area and move a hand back-and-forth across various parts of the floor or other surface areas until the inadvertently dropped item is encountered. One disadvantage of this method is that it can be time consuming if many items are dropped and scatter in many directions, and additional time can be spent searching when an item or items bounce unpredictably away from the original impact area. If the dropped item is sharp or otherwise poses a risk of contact injury, as an alternative to using the sweeping motion of an unprotected hand, one could kneel or lie down on the floor and visually look across the floor's top surface in an effort to locate it. This method also has the disadvantage of being potentially time consuming if many items are dropped and scatter in many directions, as well as when any item or items bounce unpredictably away from the original impact area. Furthermore, if the dropped item or items is medication, people taking it often have arthritis, bad knees, bad hips, a bad back, or other physical impairments and/or weakness that would prevent them from easily moving down close to a floor surface to conduct a close-up search for a dropped item, and/or prevent them from bending over more than once in an attempt to retrieve a dropped item. In addition, dropped items are frequently similar in color to that of the surface area upon which they fall, become camouflaged by colors/patterns found in and around the impact area, and/or are at least initially hidden from view (such as when they bounce under a piece of furniture), all of which complicate sweeping hand and close-to-the-floor visual searches. If the dropped item is medication, one may be concerned at the loss because of its expense, or as a result of the danger it could pose for a pet or small child. Small children, particularly infants between six and eighteen months old, are often found sitting or laying on a floor, where they investigate every inch of the floor surface close to them, as well as everything on it. At that age children also tend to pick up every small speck they encounter and place it in their mouth to taste it. Pets, particularly dogs, also exhibit similar behavior, and will show interest in any new item that has fallen onto a floor, many times attempting to eat it. In addition, glass and china used in kitchens frequently pose a hazard, since kitchen floors are rarely carpeted due to the need for frequent cleaning to remove food and other residues from them. Thus, when something breakable falls and lands on a kitchen floor, such as a glass, ceramic bowl, pitcher, or serving dish, the breakable item typically separates into an unpredictable number of small, sharp, and/or jagged shards which scatter broadly across the floor. To understand in advance the scope of the clean-up needed, and also to confirm afterward that no potentially hazardous shards remain, it would be helpful to have a device such as the projection laser scanner of the present invention that could be used in and around the suspected scatter zone to quickly determine its scope, and readily identify every broken shard needing pickup. Furthermore, if it is easily accessible, immediate use of the projection laser scanner of the present invention after glass or ceramics have been broken on a kitchen floor will be able to tell those present, which of them can safely move out of the way without getting cut or tracking hazardous shards to other areas. No other device is known for its use in this regard, or for having all of the same features and advantages as the present invention.

Tools that generate perpendicular lines of light across a floor are known in the construction industry to provide visible references that facilitate layout, and certain optical lens caps have been used to convert a single point of laser light into a laser line. Laser tools are also known and used in the construction industry for leveling, installation of floor and wall tiles, fixture installation, cabinet and shelving installation, paneling installation, masonry work, installation of pipe and conduit, and interior decoration, to name only a few common applications. One such measuring and aligning device is disclosed in U.S. Pat. No. 7,487,596 to Nash (2009) which can project a point of light and/or a fan-shaped beam that creates a line on a wall or floor. The Nash invention comprises a housing, a laser generator, and an aiming device within the housing for adjusting a position of the laser light generator. Set screws 10c (shown in the FIG. 1 of the Nash disclosure) may be used to aim the Nash laser aligning device and the Nash device may also have a mirror within its housing to make a fan-shaped beam appear virtually in the plane of the surface holding it. This is contrary to the present invention device, which must project a beam just above and substantially parallel to a surface area that is relatively flat, to reveal the location of all raised items on it by giving each of them a glowing appearance. Nash's FIG. 4b shows a laser line being formed on a raised portion of an area that is in need of being leveled out. However, Nash's FIG. 4b does not show its laser beam being positioned to also skim just over the top of the raised area to reveal other raised items further behind it and also within the projected laser light beam path. Other Nash illustrations, such as FIGS. 5b, 7a, and 7c show an internal mirror being used to create a laser light beam close to a floor surface (which the present invention does not have), and other illustrations, such as FIGS. 3a and 4a show a laser beam projected too high to be useful in quickly identifying the location of small items dropped onto the floor, while FIGS. 2b and 3b show a vertically-extending fan-shaped laser beam projected to make a line extend across the floor and also on a wall intersecting with the floor. None of these examples for possible structure and use of the Nash invention teach the structure and use of the present invention. Furthermore, the disadvantages of prior art aligning and measuring laser devices other than the Nash invention, is that they typically project a beam of light too high above a surface area to be able to detect small objects inadvertently dropped upon them, such as medication, to give them a glowing appearance so that their locations are revealed for immediate recovery. Prior art laser beam generating devices have also been used in toys and games, as play toys for cats by producing a movable spot for them to chase across a wall or a floor. However, none of the prior art laser devices are known for its configuration and use to project a beam of light with a broad field of view just above a floor surface and substantially parallel to it, and use in locating small three-dimensional items inadvertently dropped onto it and which become difficult-to-see as a result of camouflage provided by its immediate surroundings. Prior art devices typically project a beam too high above a floor surface, and should their projected beams be manually angled downwardly in an attempt to overcome this deficiency, the range of their illumination would be too drastically reduced to be effective as a rapid means of locating small items positioned on the floor surface. In contrast, the present invention has a laser positioned in a small, easily hand-manipulated, palm-sized housing such that it is able to generate a laser beam of light with a broad field of view just above a floor surface and substantially parallel to it, when it is either placed on the floor, held closely against it, attached to the lower end of a walking cane/stick, or adapted with an external mirror or other reflective surface that directs the laser beam of light with a broad field of view just above a floor surface and substantially parallel to it. When such positioning is achieved, the present invention laser beam of light reveals any irregular and raised features in the floor, but more importantly will also give all dropped items on the floor a brightly glowing appearance, including those that are too small for a person standing up to see well, or at all. This application is particularly beneficial for those with arthritis, bad knees or hips, bad backs, and/or other physical impairments or weakness, as they only need to bend over once to pick up a dropped item, and do not find themselves bending over multiple times in attempts to find it, that often become futile. Use of the present invention also helps those with children and pets, to make certain that dropped items are out of harms way. No other apparatus or method is known that has the same structure, functions in the same manner, or provides all of the safety-related and other advantages of the present invention.

BRIEF SUMMARY OF THE INVENTION

It is the primary object of this invention to provide a projection laser scanner that can be used close to a floor, or other relatively flat surface area, to easily locate all small items positioned on it, including inadvertently dropped small items that are otherwise camouflaged and not readily discernable from a standing position for their fast retrieval. A further object of this invention is to provide a projection laser scanner that can be used to quickly and easily locate very small items on floors and other relatively flat surface areas that may be harmful to children and/or pets, whether at home or in any other location. In addition, it is an object of this invention to provide a projection laser scanner that can be used to help maintain the sanitary condition of hospitals, homes, schools, restaurants, daycare facilities, laboratories, and the like, by easily locating very small pieces of unsanitary and/or infectious materials left behind after routine cleaning, dropped, or otherwise unnoticed on the floors of these and other establishments, and make them readily visible for prompt removal and proper disposal. It is also an object of this invention to provide a projection laser scanner that is lightweight for easy hand manipulation and use. Additionally, it is an object of this invention to provide a projection laser scanner that fits easily and comfortably in a person's hand, and/or which can be easily worn or carried by a person via a keychain, lanyard, or a walking cane/stick. It is a further object of this invention to provide a projection laser scanner that comprises at least one magnet for convenient mounting on a refrigerator, other kitchen appliance, desk, file cabinet, and the like, so that it is readily accessible for prompt use, and so that in addition, or in the alternative, the magnet can be used to pick up small metal items found by the broadly projected laser beam of light. It is also an object of this invention to provide a projection laser scanner that is easily and simply activated and deactivated, whether for momentary or longer periods of use. It is a further object of this invention to provide a projection laser scanner that possesses a built-in light source usable as a flashlight, to assist in searching for items where the surface area onto which a lost item is dropped is too rough and/or uneven for effective use of the present invention projection laser scanner device. Another object of this invention is to provide a projection laser scanner that has a low power indicator so that its user will know when to replace batteries for optimal use at all times.

The present invention projection laser scanner, when properly made and used, will provide a unique and innovative way to quickly find any item, no matter how small, that has been lost or accidentally dropped on a floor surface or other area and no longer remains readily visible. The present invention projection laser scanner is simply set on a relatively flat surface area, held close against it, or in some cases just above the relatively flat surface area, and when activated through use of an on-off or a momentary switch, it safely projects a brilliant colored laser beam of light with a broad field of view just above the relatively flat surface area and brightly illuminates anything in its field of view, giving any lost item positioned on the relatively flat surface area a glowing appearance, whereby it becomes instantly visible and very easy to locate and recover. The present invention beam of light can then be scanned across parts of the relatively flat surface area adjacent to the original projected laser beam path, to the left and right of it and also just above such areas, to discover whether other small items are positioned upon them, which could be a very useful application for hospitals, homes, schools, restaurants, daycare facilities, laboratories, and the like, to help them maintain their floors, countertops, tabletops, and other horizontally-extending surface areas in an optimal sanitary condition by easily locating any small piece of unsanitary and/or potentially infectious material left behind after cleaning and which otherwise would have remained unnoticed. Although several colors of laser light are currently available and can be used as a part of the present invention, and a green laser beam may be considered the brightest, a red laser light is preferred in the present invention and it is thought to have the most effective illuminating properties. Furthermore, although laser beams can be generated with different thicknesses and intensities, varying thicknesses and intensities can be used as long as they create a brilliant flowing appearance for all small objects in its path. Thus, any dropped item not otherwise readily visible against a relatively flat surface area can be immediately found and retrieved, whether it is a small tool, a very tiny screw, a lost earring, other small jewelry, vitamins, or particularly dangerous medication that could be consumed by a child or pet and create a life threatening situation. In addition, it is preferred for the present invention housing to be lightweight and have durable construction. The present invention housing should also have an easily-opened access panel that allows for prompt battery replacement. It is further contemplated for the present invention to also be easily and simply turned on and off (whether for momentary or longer durations of use), and have a housing and/or protective cover made from at least somewhat durable materials that remain presentable should it be mounted by a magnet to a refrigerator, other appliance, or a piece of furniture. Additionally, use of the laser module would be safer than most other projection lasers, as the laser beam is projected across and just above the surface of a floor, table, or other surface area, and a user's eyes would be well above it and not aligned with it so as to pose a risk of laser injury to the eyes. The present invention projection laser scanner can also be optionally adapted for additional user convenience, such as by its housing being optionally adapted to be easily worn or carried by a person via a keychain, lanyard, or a walking cane/stick, and its housing optionally incorporating at least one magnet for convenient mounting to a piece of furniture or appliance, or to use in picking up small metal items found by the present invention laser beam device, its housing optionally possessing a built-in non-laser light source to assist in searching for items where the surface area onto which a lost item is dropped is too rough and/or uneven for effective use of the laser beam, and/or its housing optionally comprising a low power indicator so that its user will know when to replace batteries for optimal performance at all times.

The description herein provides preferred embodiments of the present invention but should not be construed as limiting its scope. For example, variations in the size, number, and positioning of white LED or alternative type of lights used; the size, number, and positioning of low power indicator LED or alternative type of light used; the thickness dimension and/or perimeter configuration of its housing; the size and location of its battery compartment; and the size, number, configuration, and location of magnets, other than those shown and described herein, may be incorporated into the present invention. Thus, the scope of the present invention should be determined by the appended claims and their legal equivalents, rather than being limited to the examples given.

LIST OF COMPONENTS

Figures 1, 2:
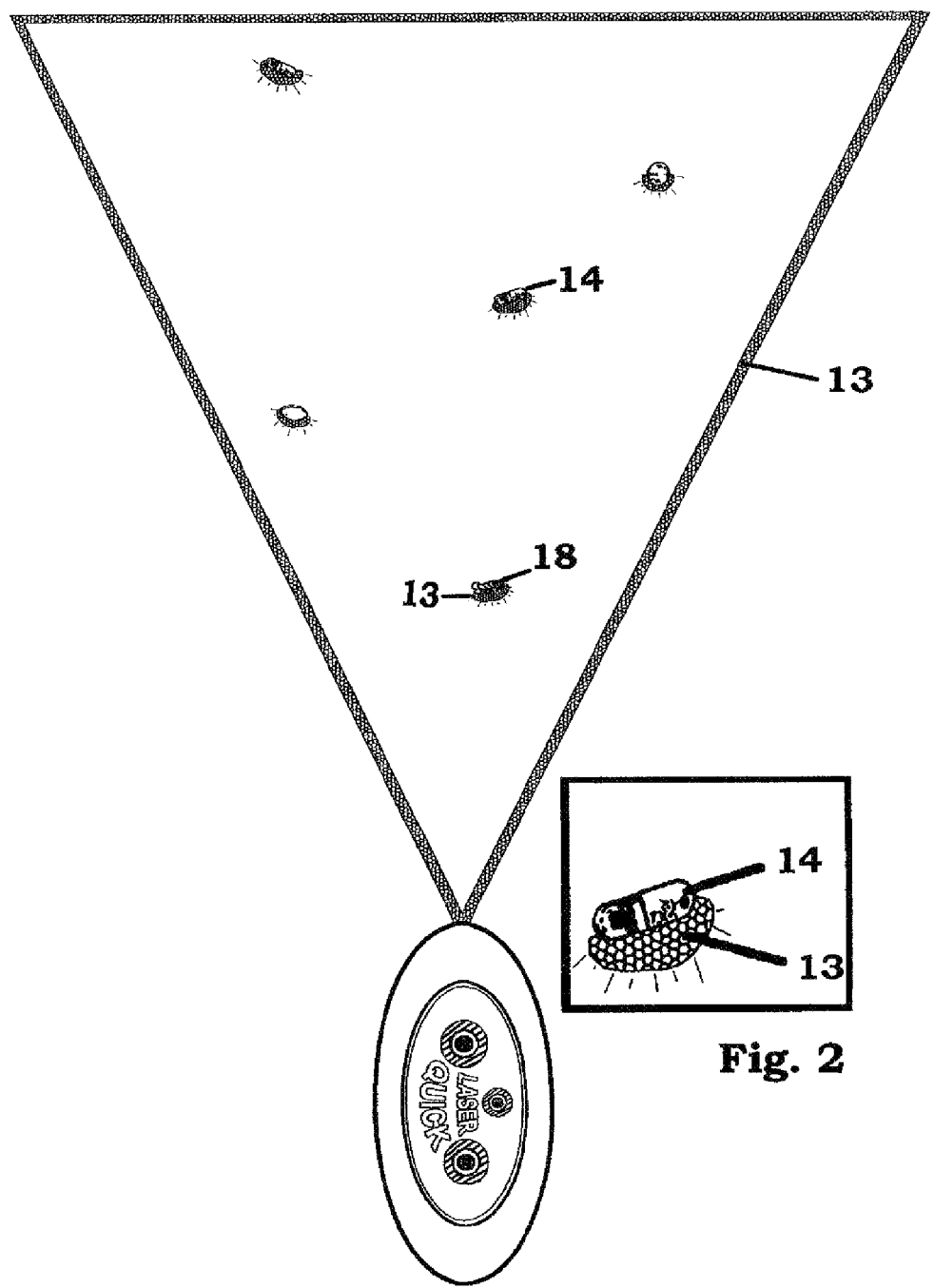
FIG. 1 is a top view of the most preferred embodiment of the present invention projection laser scanner projecting a laser beam of light having a broad field of view being projected just above a relatively flat surface area, and giving small and/or otherwise difficult-to-see three-dimensional objects (such as medication, vitamins, or a small screw) positioned on the relatively flat surface and raised above it into the path of the present invention laser beam, a brightly glowing appearance so that they become immediately revealed for prompt retrieval, with the illustration further showing illumination only the objects on the relatively flat surface area and not the relatively flat surface area its self, wherein the triangular shape extending from one end of the present invention housing is intended to represent only one possible perimeter dimension of the present invention laser beam of light having a broad field of view, which could be much larger than is shown.
FIG. 2 is a top view of a three-dimensional object brightly illuminated by the laser beam of the most preferred embodiment of the present invention, with the illumination occurring on the one side that is facing the present invention's broadly projected laser beam of light.

1—housing
2—logo plate (optional feature; plastic materials can be used)
3—LED light source (for optional flashlight and low power indicator use)
4—reflection disk (used to reflect a maximum amount of light from any LED or alternative type of light source 3 used as a flashlight or a low power indicator in up and outward directions through clear protective cover 5)
5—clear protective cover (transparency is optional, and typically present when one or more optional LED light sources are used; also of clear protective cover 5 can be movably mounted to housing 1 and used as the activation means for operating switch 10, such as but not limited to one downward movement of cover 5 against housing 1 causing activation of the two white LED lights 3 for use in a flashlight application, one additional downward movement thereafter may also activate the low power indicator blue LED light 3, along with the laser module 7 or 16, and the next/third/last downward movement of cover 5 against housing 1 thereafter may cause all lights 3 and laser module 7 or 16 to shut off).
6—larger printed circuit electronics board (used for providing mounting and electrical communication to LED or alternative type of light sources 3)
7—common laser module (projects a laser beam too high above small objects to sufficiently illuminate them for use in their prompt retrieval, and as a result needs an external mirror or reflective apparatus 15 for such applications)
8—battery compartment (may hold one or more batteries 11, according to the power requirements of the features included as a part of each present invention embodiment and the amount of operating time desired before battery replacement would be needed)
9—magnet (one or more magnets may be associated with housing 1)
10—operating switch (for activating laser module 16 and LED or alternative type of light sources 3; may be an on-off switch or a momentary switch)
11—batteries (one or more batteries may be used according to the power requirements of the features included as a part of each present invention embodiment and the amount of operating time desired before battery replacement would be needed)
12—hole opening in the logo plate 2 for LED light source 3
13—laser beam having a broad field of view and/or the glow/illumination provided thereby
14—medication or vitamin (example of small item needing retrieval)
15—mirror or other reflective apparatus (optionally used to direct a laser beam into a position close enough to a flat surface and just above it, as well as substantially parallel to the flat surface, so that the user of a common laser module 7 can locate objects by illuminating them with the projected beam of light; mirror or other reflective apparatus 15 can be configured as a detachable external accessory for housing 1)
16—present invention laser module configured for independently creating a laser beam of light with a broad field of view just above a relatively flat surface area and substantially parallel to it, without the need for an internal or external mirror or other reflective apparatus 15
17—electrical wiring (used inside housing 1 for electrical communication between selected components)
18—small screw (example of small item needing retrieval)
19—smaller printed circuit board (connected to batteries 11 in battery compartment 8 and used to provide electrical connection between laser module 16 and operating switch 10, as well as electrical connection between operating switch 10 and the larger printed circuit electronics board 6 that is employed in larger palm-sized embodiments for providing mounting and electrical communication for LED or alternative type of light sources 3)

DETAILED DESCRIPTION OF PREFERRED EMBODIMENTS

The present invention comprises a projection laser scanning device and method of its use wherein it can be set down upon, or held closely against, the top of a relatively flat surface area (level or not), such as but not limited to a floor, countertop, tabletop, and the like, and wherein after the activation of its operating switch 10, the present invention laser module 16 creates a laser beam of light with a broad field of view 13 that is projected substantially parallel to the relatively flat surface area, and just above it, to illuminate all raised items in its path (such as but not limited to the medication 14 and small screw 18 shown in FIG. 1) and give each a glowing appearance, making them immediately identifiable for prompt recovery. It is not critical whether the laser module of the present invention creates the glowing effect via use of a lens cap that broadens a laser dot into a line, or via use of a dot laser that is spinning or being moved in a sweeping action back and forth across its field of view. Furthermore, use of the present invention projection laser scanning device does not present a safety risk to eyes during its proper use, as it is employed very close to a surface area that is in a lowered position relative to the user's eyes. Should a surface area upon which a small object has been dropped and needs prompt recovery be close to a persons' eyes, the object would be more readily visible and use of the present invention would not likely be needed. Areas adjacent to the original light path projected by the present invention projection laser scanner can also be quickly and easily viewed for the presence or absence of small raised objects by moving the projected laser beam of light to the right and left toward them. Thus, with use of the present invention, the locations of inadvertently dropped items/objects (14, 18, and other) that would otherwise be camouflaged and hidden from view by colored/patterned surroundings, become instantly identified as a result of the vivid and brilliant illumination of them created by the broadly projected present invention laser beam of light 13. Although not critical, a red laser is preferred in present invention use, as it creates a very vivid illumination effect. Furthermore, the laser used in the present invention embodiments is not limited to a single beam width or intensity. If the relatively flat surface area upon which a small item has fallen has no raised surface texture or other surface irregularity, no part of the relatively flat surface area will be illuminated, and only the dropped item or items on it will be given a glowing appearance (see FIG. 1). In the alternative, although not shown in the accompanying illustrations, should the relatively flat surface area upon which a small item has fallen have some raised feature or irregularity, the raised features and irregularities present will also be illuminated by the broadly projected present invention laser beam of light 13, however, the small item or items being sought will also be very evident, instantly recognizable, and easy to retrieve. Optionally the projection laser scanner device of the present invention can have many variations, including but not limited to a magnet 9 associated with its housing and usable for mounting the housing for ready accessibility against the front or side of a refrigerator, other kitchen appliance, metal desk or file cabinet, and the like. Magnet 9 may also assist a user in picking up small metal items located by the present invention's laser beam of light 13. Another option for the present invention projection laser scanner device is one or more LED or other light sources 3 that can be used as a low power indicator to make certain that the device will always have fresh batteries for optimal performance when needed, or use as a flashlight to search for difficult-to-see small items where the relatively flat surface area onto which they have been dropped is too rough and/or uneven for effective use of the present invention's laser beam of light 13. An additional option, although not shown, can be the connection of the present invention housing 1 to a keychain, lanyard, or a walking cane/stick, so that it can be easily carried, worn, and employed by its user.

Figure 3:
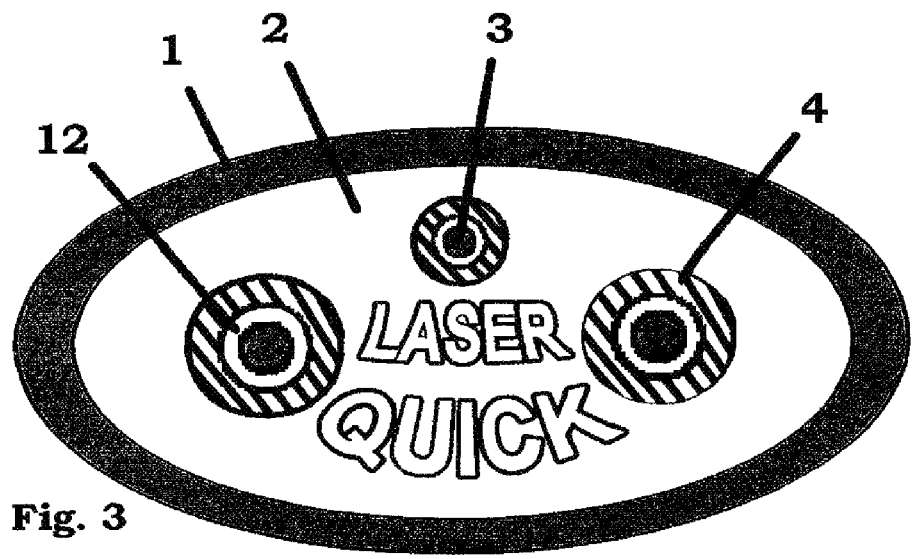
FIG. 3 is a top view of the housing in the most preferred embodiment of the present invention projection without its cover and the logo plate having two LED light sources and a low power indicator LED light extending upwardly through it via separate hole openings, with the two LED light sources and the low power indicator LED light each having a separate reflection disk around them.
Figure 4:
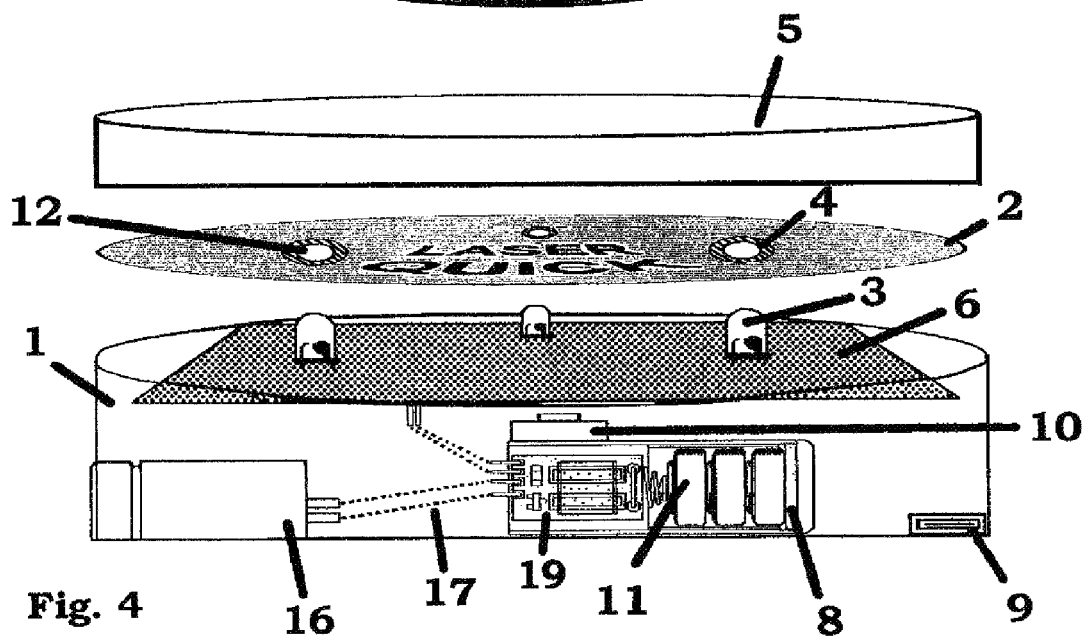
FIG. 4 is an exploded view of the most preferred embodiment of the present invention from one of its sides and having a housing, a clear protective cover above the housing the entirety of which can also be the source of activation for the laser module, the LED light sources and a low power indicator LED light, a logo plate positioned between the housing and its protective cover, two LED light sources and a low power indicator LED light connected to the first/larger printed circuit electronics board, the first/larger printed circuit electronics board positioned under the logo plate, an opening in the logo plate for each LED light source and the low power indicator LED light, a reflection disk adjacent to each opening in the logo plate, an activation switch (for on-off or momentary operation of the laser module, LED light sources, and low power indicator LED light), a battery compartment with multiple batteries in electrical communication with a second/smaller printed circuit electronics board, a laser module, a magnet, and electrical wiring connecting both the laser module and the first/larger printed circuit electronics board to the second/smaller printed circuit electronics board.

For both clarity and brevity in the ensuing description, hereinafter when the words "floor" or "floor surface area" are mentioned, a list of alternative or related surface areas such as countertops, tabletops, and the like will not always be mentioned. Therefore, unless otherwise stated, it should be assumed that the same applications and or actions specifically mentioned for a floor or floor surface area can also relate to other relatively flat and horizontally-extending surface areas. In addition, it should be further understood and recognized that it is considered within the scope of the present invention that its inspection/retrieval applications are not only limited to horizontally-extending surface areas. Also, while medication or a vitamin 14 and a small screw 18 are shown in the illustrations as examples of small items potentially in need of retrieval, many other objects could also be located by the broadly projected present invention laser beam of light 13, including but not limited to contact lenses, small tools, pins, needles, push pins, coins, beads, staples, paper clips, broken glass, rings, earrings, other jewelry, and individual gemstones separated from jewelry. FIGS. 1 and 2 show medication or a vitamin 14 and a small screw 18 brightly illuminated by the broadly projected present invention laser beam of light 13. FIGS. 3-4 show more detail about the most preferred embodiment of the present invention projection laser scanner, while FIGS. 5-7 show laser modules 7 and 16 in medication 14 locating applications.

Figure 5:
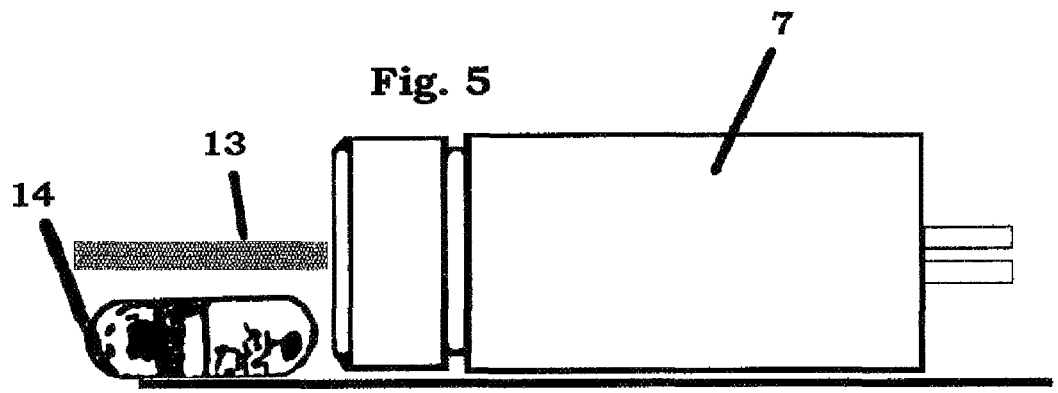
FIG. 5 is a side view of a common laser module that is configured to project a beam too high above a relatively flat surface area to give small objects a glowing appearance for instant identification of their locations, but which is still usable as a part of the present invention with the assistance of an external mirror or other reflective apparatus, as shown in FIG. 7 below.
Figure 6:
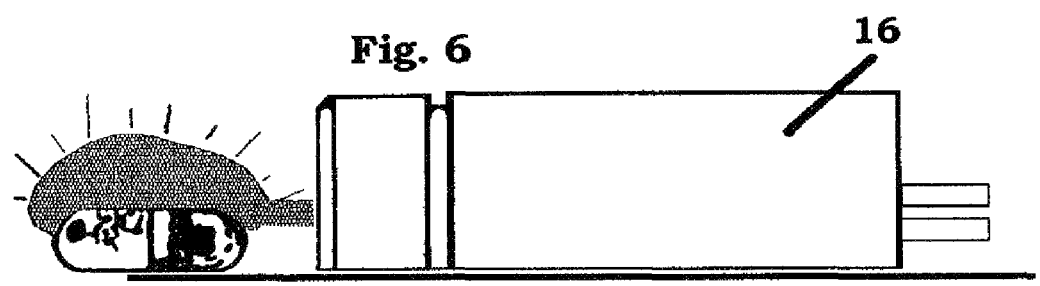
FIG. 6 is a side view of a laser module that is configured to project a beam just above a relatively flat surface area and illuminate small objects thereon, giving them a glowing appearance for instant identification of their locations.

FIG. 1 is a top view of the most preferred embodiment of the present invention projection laser scanner device projecting a laser beam of light 13 in front of it, which has a broad field of view and is also projected just above a relatively flat surface area (not given a numerical identification, but shown in FIGS. 5 and 6 under laser modules 7 and 16, respectively). FIG. 1 also shows several small and/or otherwise difficult-to-see three-dimensional objects (such as medication 14 or a small screw 18) positioned on the relatively flat surface area and raised above it into the path of the broadly projected laser beam of light 13, which gives them a bright glowing appearance that allows them to become immediately identifiable for prompt retrieval. FIG. 1 further shows only the raised objects (14 and 18) on the flat surface having illumination, and not any portion of the relatively flat surface area itself. The triangular representation extending from one end of the present invention housing (given the number 1 in FIG. 4) simply defines one example of an approximate perimeter dimension for broadly projected laser beam of light 13, which could be much larger or longer than shown. FIG. 2 is a top view of a three-dimensional object (medication or a vitamin 14) brightly illuminated by the present invention laser beam of light 13, with the illumination occurring on the one of its sides facing the laser beam of light 13 projected from the present invention, as also shown in FIG. 1. The perimeter configuration of housing 1 is not limited to that shown in FIG. 1. However, it is preferred for housing 1 to be lightweight, have relatively durable construction, and have a configuration comfortable to an adult human hand so that it can be easily grasped and used, although it can be configured even smaller for keychain use. Furthermore, although FIG. 1 shows the present invention laser beam of light 13 extending from one end of housing 1, the part of housing 1 shown for projection of laser beam of light 13 should not be considered as limiting. In the alternative, FIG. 1 could also represent the scanning result of a motorized spinning or sweeping motion dot laser.

FIGS. 3-4 show more detail about the most preferred embodiment of the present invention projection laser scanner. FIG. 3 is a top view of the housing 1 in the most preferred embodiment of the present invention projection without its cover 5 and the logo plate 2 shown having two LED light sources 3 (typically white and used as a flashlight on non-flat surface areas where the present invention laser beam of light 13 may not be sufficient for locating small objects) and a third centrally-located LED light source 3 (typically blue and used as a low power indicator). Although not marked in the illustrations, it is preferred that the two LED light sources 3 (to be used as a flashlight) comprise bright LED light sources that create white light, and for the third centrally-located LED light source 3 (to be used as a low power indicator) comprise an LED light source that creates colored light, such as but not limited to blue light. FIG. 3 shows each LED light source 3 extending upwardly and centrally through a separate hole opening 12 in logo plate 2, with each LED light source 3 also being surrounded by a reflection disk 4 that is used to reflect a maximum amount of light from LED light sources 3 in up and outward directions through clear protective cover 5. Although LED light sources 3 extend through hole openings 12 in logo plate 2 and the reflection disks are typically secured to logo plate 2, the LED light sources 3 are not connected to logo plate 2. Instead, all LED light sources 3 used are physically and electrically connected to first/larger printed circuit electronics board 6, as shown in FIG. 4. FIG. 4 is an exploded view of the most preferred embodiment of the present invention as shown from one of its sides and having a housing 1, a clear protective cover 5 positioned above housing 1 the entirety of which can also be the source of activation for the laser module, the logo plate 2 shown in FIG. 3 positioned between housing 1 and protective cover 5, three LED light sources 3 connected to a first/larger printed circuit electronics board 6, and the first/larger printed circuit electronics board 6 being positioned under logo plate 2. Although not limited thereto, in the most preferred embodiments of the present invention, housing 1, protective cover 5, and logo plate 2 are made from plastic materials. FIG. 4 also shows a hole opening 12 in logo plate 2 for each laterally-positioned LED light source 3 connected to first/larger printed circuit electronics board 6 for use as a flashlight and the positioned LED light source 3 centrally connected to first/larger printed circuit electronics board 6 for use as a low power indicator. In addition, FIG. 4 shows a reflection disk 4 adjacent to each hole opening 12 in logo plate 2, as mentioned above for use in maximizing light output from LED light sources 3 through clear protective cover 5. Should a present invention embodiment not comprise the optional LED light sources 3, then protective cover 5 does not need to have transparent properties. Within housing 1, FIG. 4 shows an activation switch (for on-off or momentary operation of the laser module 16 and LED light sources 3), a battery compartment 8 with multiple batteries 11 in electrical communication with a second/smaller/compact printed circuit electronics board, a laser module 16, a magnet 9, and electrical wiring 17 providing electrical communication between laser module 16 and second/smaller/compact printed circuit electronics board 19, as well as between first/larger printed circuit electronics board 6 and second/smaller/compact printed circuit electronics board 19. FIG. 4 shows the batteries 11 and operating switch 10 in electrical communication with compact printed circuit electronics board 19. As previously mentioned, operating switch 10 may be an on-off switch, or a momentary switch, but it is not limited thereto. Also, although not limited thereto, when clear protective cover 5 is movably mounted to housing 1 and used as the activation means for operating switch 10, one downward movement of cover 5 against housing 1 may activate the two white LED lights sources 3 for use in a flashlight application, one additional downward movement thereafter may also activate the low power indicator blue LED light source 3, along with the laser module 7 or 16, and the next/third/last downward movement of cover 5 against housing 1 thereafter may cause all LED lights sources 3 and laser module 7 or 16 to shut off. The number, shape, dimension, and location of LED light sources 3, battery compartment 8, and magnet 9 are also not limited to that shown in FIG. 4. Furthermore, the number of batteries 11 may be different from that shown in FIG. 4 as long as they complement the number, size, and shape of batteries required by the battery compartment or compartments 8 used within housing 1. It should also be noted that the electrical wiring 17 shown in FIG. 4 is merely representative, and may be different from that illustrated and should not be considered as limiting. Although not shown, it is contemplated for batteries 11 to be replaced, and housing 1 would be expected to have means for easy access to batteries 11 for such purposes.

Figure 7:
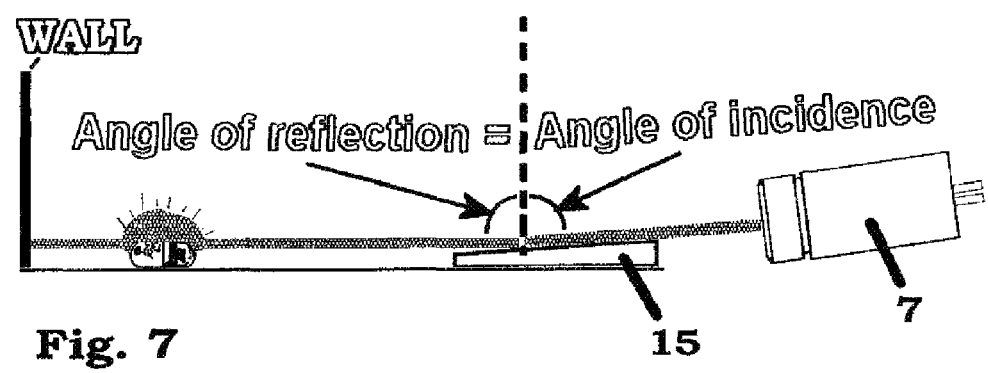
FIG. 7 is a side view of a common laser module usable as part of an alternative embodiment of the present invention which further comprises the use of an external mirror or other reflective apparatus to reposition the broadly projected beam of laser light just above a relatively flat surface area so as to identify the locations of multiple small items scattered across it, with the mirror or other reflective apparatus preferably being the form of an external attachment, although not specifically shown as such.

FIGS. 5-7 show laser modules 7 and 16 in locating applications for medication or a vitamin 14. FIG. 5 is a side view of a common laser module 7 that unassisted would project a beam too high above a relatively flat surface area to give small objects (such as medication 14) a brightly glowing appearance for instant identification of their locations, but which can be usable as a part of the present invention with the assistance of an external mirror 15 or other reflective apparatus, as shown in FIG. 7. FIG. 6 is a side view of a specially configured present invention laser module 16 that is designed, shaped, and equipped with a wide-angled lens to project a broadly-directed laser beam of light 13 just above a relatively flat surface area without the use of a mirror 15 and thereby illuminate small objects (14, 18, and other) on the relatively flat surface area, giving each one of them a brightly glowing appearance for instant identification of their locations. Laser module 16 is shown positioned within the hollow interior of housing 1 and longitudinally aligned with housing 1, also being in close proximity to the bottom interior surface of housing 1 and configured and positioned to project its broad laser beam of light 13 beyond housing 1 in a plane just above and substantially parallel to the bottom interior surface of housing 1. FIG. 7 is a side view of a commonly available laser module 7 usable as part of an alternative embodiment of the present invention which must be employed with an external mirror 15 or other reflective apparatus to reposition the broadly projected beam of laser light 13 just above a relatively flat surface area and very close to it to be able to identify the locations of multiple small items scattered across it. Optionally, although not shown, the mirror 15 or other reflective apparatus can be in the form of an external attachment or accessory to housing 1. As shown in FIG. 6, and also shown in FIG. 1, it is critical for the present inventions broadly-directed laser beam of light 13 to be projected at a height just above a relatively flat surface area that allows it to brightly illuminate any small object (such as but not limited to medication 14 or small screw 18) in its path, but which also may in at least in part pass over the small object to reveal other similarly small objects located at a greater distance from housing 1. In contrast, FIG. 4*b* of the Nash disclosure shows a laser beam creating a line on a raised area needing to be leveled, but does not allow the laser beam to reach beyond the raised area for locating other areas of interest. Thus, use of the present invention rapidly locates any important item inadvertently dropped so that it can be promptly retrieved, as well as simultaneously locating many other items scattered across a relatively flat surface area that may have bounced unpredictably away from the original impact site. Should investigation of areas adjacent to the first projected path of the present invention laser beam of light 13 be needed, a user needs only to move housing 1 to the right or the left of the original projected path, or farther away from the original location of housing 1 along the same or similar axis as that of the original projected path to give all small objects present a brightly glowing appearance.

Use of the present invention saves time in locating inadvertently dropped small objects that blend in against background surroundings and become difficult to see. One can set housing 1 on a relatively flat surface area, or hold housing 1 close to the relatively flat surface area, press on the protective cover 5 to activate operating switch 10 and see what small items have become illuminated by a broadly projected laser beam of light 13. If no objects of interest are found, the user could move, tilt, rock, tip, or otherwise maneuver housing 1 to see if any objects not previously seen are thereafter revealed. Another option, although not shown, is to attach housing 1 to the bottom of an elongated handle, cane, walking stick, and the like, wherein the present invention laser beam of light 13 can be activated and/or moved into new directions/orientations through use of the handle. This would be helpful to people with bad backs, bad hips, bad knees, dizziness, and other conditions that prevent one from easily bending over. The present invention method also has the potential for providing time savings when many items are dropped and scatter in differing directions, and also when an item or items bounce unpredictably away from the original impact area. Furthermore, if the dropped item or items is medication, people taking it often have arthritis, bad knees, bad hips, a bad back, or other physical impairments and/or weakness that would prevent them from easily moving down to a floor surface to conduct a close-up search for a dropped item, or even bending over more than once in an attempt to retrieve a dropped item. The present invention would assist them in doing so. In addition to finding dropped medication, there are many important safety applications of the present invention projection laser scanner, which include but are not limited to, finding contact lenses, eyeglass screws, small tools, pins, needles, push pins, coins, beads, staples, paper clips, vitamins, and other objects that one would not want a baby, small child, or pet to find and swallow; broken glass or ceramic shards that could cause injury to people and pets; expensive rings, earrings, and/or gemstones inadvertently separated from jewelry that a small child or pet could also find and swallow; and countless other items that can easily blend into and become camouflaged by background surroundings. Furthermore, when a breakable item, such as glass, falls and lands on a floor or other hard surface area, it typically separates into an unpredictable number of small and/or sharp/jagged shards which scatter broadly across the hard surface area. To understand in advance the scope of the clean-up needed, and also to confirm afterward that no potentially hazardous shards remain, it would be helpful to use the projection laser scanner of the present invention in and around the suspected scatter zone to quickly determine its scope, and readily identify every broken shard needing pickup. Furthermore, if it is easily accessible, immediate use of the projection laser scanner of the present invention after glass has been broken on a hard floor will be able to tell those present who can safely move out of the way without getting cut or tracking hazardous shards to other areas.

What is claimed is:

1. A self-contained and fully portable projected scanning laser device in combination with at least one camouflaged and otherwise difficult-to-see small three-dimensional object laying on a relatively flat surface at an unknown variable distance away from a user of said device, with said device projecting a laser beam closely above the relatively flat surface while touching little of the surface itself, the beam very vividly illuminating each camouflaged and otherwise difficult-to-see small three-dimensional object and causing it to brightly glow only as a result of direct contact with the projected laser beam of light for immediate identification of object location and easy retrieval thereof, said projected scanning laser device comprising:
   a small and lightweight housing configured for easy grasping by a human adult hand, said housing also having a substantially planar bottom interior surface;
   a laser module within said housing, said laser module located in close proximity to and substantially parallel with said substantially planar bottom interior surface of said housing so as to become longitudinally aligned therewith, while also configured and positioned to project a laser beam of light with a broad field of view beyond said housing in a plane just above and very close to said bottom interior surface, the beam oriented and positioned to make contact primarily with at least one small three-dimensional object located on a relatively flat surface when said bottom interior surface of said housing is very closely aligned with the flat surface, the projected beam causing each object it contacts to become very vividly illuminated and glow brightly while concurrently contacting very little of the relatively flat surface supporting the object;
   activation means associated with said housing and adapted for causing said laser module to project a laser beam of light with a broad field of view;
   at least one battery compartment located within said housing and containing at least one battery; and
   electrical connection means adapted for electrically interconnecting said activation means, said laser module, and said at least one battery to provide electrical power from said battery to said laser module after said activation means is engaged and thereby permit said laser beam with a broad field of view to be projected beyond said housing;
   wherein said housing further comprises at least one light source configured and positioned to project a beam of light with a broad field of view beyond said housing and onto a non-flat surface, the beam sufficiently bright to illuminate the non-flat surface and small three-dimensional objects supported by the non-flat surface.

2. The device of claim 1 further comprising a printed circuit electronics board positioned within said housing and said at least one light source connected to said printed circuit electronics board.

3. The device of claim 1 wherein said electrical connection means comprises at least one compact printed circuit electronics board in electrical communication with said activation means, said laser module, and said at least one battery.

4. The device of claim 2 further comprising a light-transmissive cover, and also comprising a reflection disk configured and positioned within said housing to assist the travel of light emitted from said at least one light source through said cover.

5. The device of claim 1 further comprising at least one low power indicator light associated with said housing and connected to said at least one battery, said low power indicator light positioned for visibility from outside said housing.

6. The device of claim 1 further comprising at least one magnet associated with said housing.

7. The device of claim 6 wherein said at least one magnet is selected from a group consisting of magnets configured and positioned relative to said housing for easy retrieval of small three-dimensional objects having magnetic properties, and magnets having sufficient magnetic strength to attach said housing and the remaining portions of said device to a vertically-extending surface having magnetic properties.

8. The device of claim 7 wherein said activation means for said laser module comprises at least one cover associated with said housing.

9. The device of claim 1 further comprising tool means adapted for placement of said housing close to a relatively flat surface adjacent to a user of said device without the user having to bend over.

10. The device of claim 9 a further configured for activation of said laser module via said tool means.

11. The device of claim 9 wherein said tool means is selected from a group consisting of elongated handles, canes, and walking sticks.

12. A method of using the device of claim 1 to locate objects otherwise camouflaged and hidden by their surroundings, said method comprising the steps of:
provliding the device of claim 1, a relatively flat surface area, and at least one small three-dimensional object that blends in and is difficult-to-see when placed upon said relatively flat surface area;
placing said at least one three-dimensional object onto said relatively flat surface area;
placing said device of claim 1 above and in close proximity to said relatively flat surface area so that a laser beam of light with a broad field of view projected from said laser module will extend beyond said housing in a plane just above and substantially parallel to said relatively flat surface area; and
engaging said activation means to cause said laser beam of light with a broad field of view to be projected beyond said housing, and when said projected laser beam of light with a broad field of view contacts said at least one small three-dimensional object, it becomes very vividly illuminated with a brightly glowing appearance that allows it to be instantly located.

13. The method of claim 12 wherein said housing further comprises at least one light source configured and positioned to project a beam of light with a broad field of view beyond said housing and onto a non-flat surface, and the step of directing the beam to illuminate the non-flat surface and any small three-dimensional objects supported by the non-flat surface.

14. The method of claim 13 further comprising a printed circuit electronic board positioned within said housing and at least one light source connected to said printed circuit electronics board, and further comprising the step of using the beam of light emitted from said at least one light source to search for objects on non-flat surface areas where said laser beam of light with a broad field of view is less effective.

15. The method of claim 14 further comprising a light-transmissive cover and a reflection disk configured and positioned within said housing to assist the travel of light emitted from said at least one light source through said cover.

16. The method of claim 12 further comprising tool means adapted for placement of said housing close to a relatively flat surface adjacent to a user of said device without the user having to bend over and a step of attaching said tool means to said housing, said step of attaching occurring prior to said step of placing.

17. The method of claim 16 wherein said tool means is selected from a group consisting of elongated handles, canes, and walking sticks.

18. The method of claim 12 further comprising at least one magnet associated with said housing, and the step of using said magnet to rapidly gather and pick up small metallic objects located by said laser beam of light with a broad field of view.

19. The method of claim 18 further comprising the step of providing a vertically-extending surface with magnetic properties, wherein said magnet also has sufficient magnetic strength to attach said housing and the remaining portions of said device in claim 1 to said vertically-extending surface, and the step of using said magnet to attach said housing to said vertically-extending surface.

\* \* \* \* \*